United States Patent [19]

O'Shaughnessy

[11] 4,450,712
[45] May 29, 1984

[54] PULP CONSISTANCY MEASUREMENT

[75] Inventor: Kevin O'Shaughnessy, Widenham, South Africa

[73] Assignee: Brenda O'Shaughnessy, Widenham, South Africa

[21] Appl. No.: 313,068

[22] Filed: Oct. 19, 1981

[30] Foreign Application Priority Data

Dec. 11, 1980 [ZA] South Africa ............... 80/7753

[51] Int. Cl.³ ........................................... G01N 15/04
[52] U.S. Cl. ..................................... 73/61 R; 73/438
[58] Field of Search ................... 73/61 R, 55, 438

[56] References Cited

U.S. PATENT DOCUMENTS

| 1,963,011 | 6/1934 | Albersheim et al. | 73/55 |
| 3,528,281 | 9/1970 | Cowan | 73/61 R |
| 3,535,917 | 10/1970 | Blair et al. | 73/55 |
| 3,548,638 | 12/1970 | Uchida et al. | 73/55 |

FOREIGN PATENT DOCUMENTS 1168123  4/1964  Fed. Rep. of Germany ......... 73/55

Primary Examiner—S. Clement Swisher
Assistant Examiner—Joseph W. Roskos
Attorney, Agent, or Firm—Ladas & Parry

[57] ABSTRACT

Apparatus is provided for measuring the concentration of particulate or fibrous material in a fluid flow in part of a flow line. The concentration is measured by detecting the recovery pressure downstream of a pressure reducing unit.

6 Claims, 1 Drawing Figure

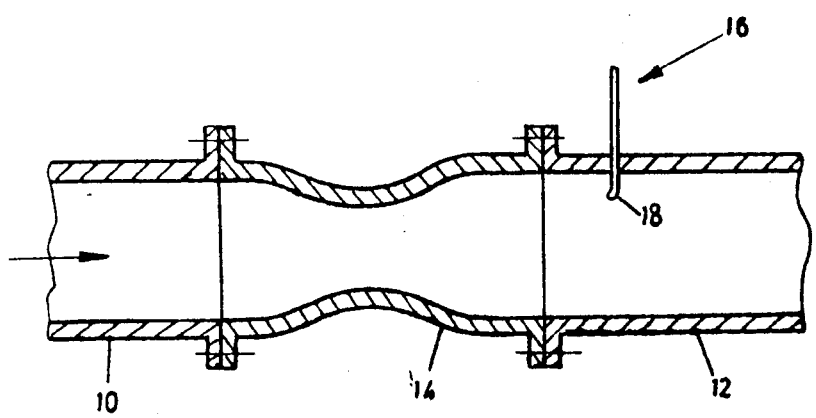

PULP CONSISTANCY MEASUREMENT

The invention relates to process measuring apparatus.

It is known that when passing fluid through a pressure reducing unit, such as a venturi, there is a pressure reduction in the venturi and a pressure recovery downstream of the reducing unit. In accordance with the configuration of the unit and the type of fluid passing therethrough, the degree of pressure recovery can be reasonably predicted.

According to one aspect of the present invention a method of determining the concentration of particulate or fibrous material in a fluid comprises flowing the fluid through a pressure reducing unit and measuring the recovery pressure downstream of the unit.

According to another aspect of the invention apparatus for determining the concentration of particulate or fibrous material in a fluid comprises a flow line through which the fluid can be passed, a pressure reducing unit in the flow line and means for measuring the recovery pressure of the fluid downstream of the reducing unit.

A method according to the invention will now be described with reference to the accompanying schematic drawing which shows part of a supply line for paper pulp slurry in cross section.

Referring to the drawing, part of a flow line comprises pipes 10 and 12 with a venturi pressure reducing unit 14 coupled between the pipes 10 and 12.

A pressure sensor 16 having a probe 18 is fitted to the pipe 12 downstream of the unit 14. In use, paper pulp slurry is flowed through the flow line and the pressure of the fluid measured by the sensor 16.

It was earlier known that the pressure of various fluids recovered after passage through a pressure reducing unit, such as a venturi. For example water will recover to around 80% of the pressure at the inlet of a venturi. However it was not previously realised that concentrations of solids in a liquid, such fibrous pulp in a water, could accurately be determined by measuring the recovery pressure. In paper slurry for example it is necessary to treat the slurry in later processing to produce paper in accordance with the concentration of pulp present.

Normally, a concentration of 4% paper pulp to water by volume is used as the paper pulp slurry. Small variations in this concentration can dramatically affect the qualtity of paper produced. Further, it is important to know by how much the concentration has altered in the slurry being used so that measured compensations can be made up-stream of the unit 14 to correct the concentration and/or downstream to vary the later chemical and physical processing of the slurry in the paper making plant.

Hitherto, using shear type sensing instruments for example for detecting pulp concentration only comparative measurements were possible so that difficulties could arise in determining how and particularly to what extent rectifying adjustments must be made.

Normally, the rate of flow of the slurry is kept constant but it may change and in such a case the apparatus described is provided with a rate of flow measuring device (not shown) to monitor the rate of flow in the region of the unit 14. Such rate of flow signals are required to provide computation of the pressure measure to compensate for any changes of flow. Alternatively, or in addition, a pressure sensing probe may be placed in the flow line upstream of the unit 14 to provide a reference pressure signal, if desired.

Further, the flow line shown may be placed conveniently in a by-pass of the main flow line supplying the paper mill. In which case the rate of flow can if preferred be kept constant even if the main flow rate varies to some extent from time to time.

Whereas, the invention has been described with reference to a paper pulp slurry, in other embodiments concentrations of particulate or fibrous material in liquids can be determined by monitoring the recovery pressure of fluid flowing in a flow passage downstream of a pressure reducing unit. The shape and configuration of that unit can be varied as required in accordance with the type of fluid used and the range of concentrations to be measured.

I claim:
1. A method of determining the concentration of particulate or fibrous material in a fluid comprising:
   (a) a flowing of the fluid at a velocity to cause turbulence to the particulate or fibrous material in the fluid through a pressure reducing unit with high level of recovery of pressure drop downstream thereof;
   (b) measuring the pressure upstream of the unit;
   (c) measuring the recovery pressure downstream of the unit;
   (d) comparing the above measurements with a constant to determine the concentration of the particulate or fibrous material.

2. A method according to claim 1 which includes an additional step of compensation of the measured pressure upstream of the pressure reducing unit.

3. A method according to claim 1 in which the pressure reducing unit is positioned in a by-pass of a main flow for the fluid.

4. Apparatus for determining the concentration of particulate or fibrous material in a fluid comprising:
   (a) flow line through which fluid can be passed at a velocity to cause turbulence to the particulate or fibrous material in the fluid;
   (b) a pressure reducing unit in the flow line with a high level of recovery of a pressure drop downstream thereof;
   (c) means for measuring the pressure upstream of the unit; and
   (d) means for measuring the recovery pressure of the fluid downstream of the reducing unit.

5. Apparatus according to claim 4 including means for providing pressure compensating signals in response to the pressure measurements.

6. Apparatus according to claim 4 including a by-pass for a main flow of the material, and the pressure reducing unit being positioned on said by-pass.

* * * * *